(12) United States Patent
Long et al.

(10) Patent No.: US 11,999,667 B2
(45) Date of Patent: Jun. 4, 2024

(54) CILIATED PROTOZOAN WITH THE EFFECT OF PROMOTING PLANT SEED GERMINATION AND SEEDLING GROWTH

(71) Applicant: OCEAN UNIVERSITY OF CHINA, Qingdao (CN)

(72) Inventors: Hongan Long, Qingdao (CN); Yurou Jiang, Qingdao (CN); Haichao Li, Qingdao (CN); Jiao Pan, Qingdao (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

(21) Appl. No.: 18/330,402

(22) Filed: Jun. 7, 2023

(65) Prior Publication Data

US 2024/0002307 A1 Jan. 4, 2024

(30) Foreign Application Priority Data

Jun. 9, 2022 (CN) .......................... 202210648748.7

(51) Int. Cl.
- *C05F 11/08* (2006.01)
- *A01G 7/06* (2006.01)
- *C12N 1/10* (2006.01)
- *C12R 1/90* (2006.01)

(52) U.S. Cl.
CPC ................ *C05F 11/08* (2013.01); *A01G 7/06* (2013.01); *C12N 1/105* (2021.05); *C12R 2001/90* (2021.05)

(58) Field of Classification Search
CPC .......... C05F 11/08; A01G 7/06; C12N 1/105; C12R 2001/90
See application file for complete search history.

(56) References Cited

PUBLICATIONS

Zhang Wen-Li, et al., The ciliate protozoan Colpoda cucullus can improve maize growth by transporting soil phosphates, Journal of Integrative Agriculture, 2022, pp. 855-861, vol. 21 No. 3.

*Primary Examiner* — David Browe
(74) *Attorney, Agent, or Firm* — Bayramoglu Law Offices LLC

(57) ABSTRACT

A method of using a strain of ciliated protozoan for promoting effect on germination and growth of plant seeds is provided. The ciliated protozoan is a *Colpoda* species JH2-5-4, with preservation number of China Center for Type Culture Collection ("CCTCC") NO. C202229. A method of screening and selecting a highly efficient and active strain suitable for use as a microbial fertilizer in plant cultivation is provided. The selected ciliated protozoan strain shortens the germination time of plant seeds, promotes plant growth, and improves seedling survival rate.

1 Claim, 6 Drawing Sheets
Specification includes a Sequence Listing.

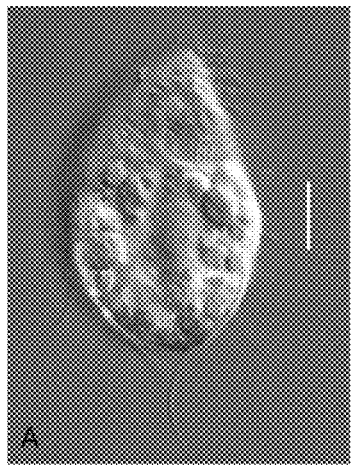
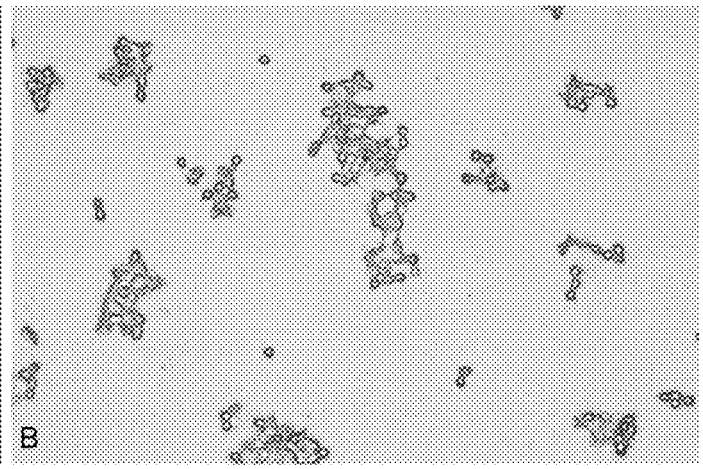
FIG. 1A                     FIG. 1B
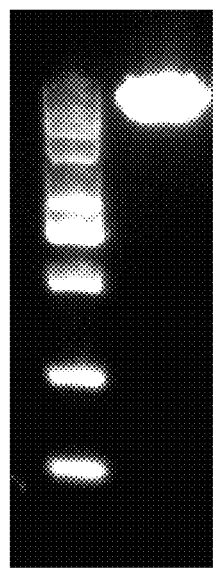
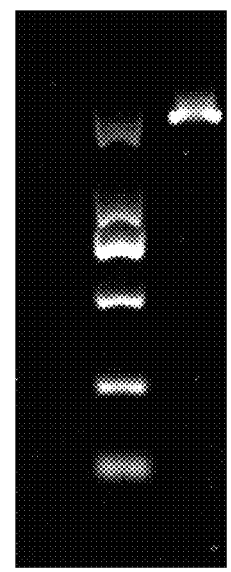
FIG. 2                      FIG. 3

CILIATED PROTOZOAN WITH THE EFFECT OF PROMOTING PLANT SEED GERMINATION AND SEEDLING GROWTH

CROSS REFERENCE TO THE RELATED APPLICATION

This application is based upon and claims priority to Chinese Patent Application No. 202210648748.7, filed on Jun. 9, 2022, the entire content of which is incorporated herein by reference.

SEQUENCE LISTING

The instant application contains a Sequence Listing which has been submitted in XML format via EFS-Web and is hereby incorporated by reference in its entirety. Said XML copy is named GBBJSR001-PKG-Sequence-Listing.xml, created on Jun. 16, 2023, and is 9,895 bytes in size.

TECHNICAL FIELD

The present invention belongs to the technical field of microbial fertilizers, and specifically relates to a ciliated protozoan with the effect of promoting plant seed germination and seedling growth.

BACKGROUND

As a major agricultural country, China has a total area of grain sowing of approximately 1.764 billion mu, accounting for about 7% of the world's existing cultivated land area. As a guarantee of grain production, fertilizers play an important role in China's agricultural production process, with an annual production of fertilizers of up to 53.958 million tons. However, excessive use of fertilizers can lead to agricultural pollution, soil degradation, water source pollution, and threaten the environment and human health. Therefore, the rational use of fertilizers has also received increasing attention. The development of microbial fertilizers and other organic fertilizers to replace chemical fertilizers has become one of the research hotspots in agriculture.

Microbial fertilizers, also known as microbial bacterial fertilizers, mainly consist of actinomycetes, phototrophic bacteria, *Bacillus*, phosphorus and potassium decomposing bacteria, etc. The functional microorganisms in microbial fertilizers can consume and utilize domestic garbage and agricultural pollutants, increase soil fertility, improve soil conditions, and reduce environmental pollution. Currently, the cumulative application area of microbial fertilizers in China is only 300 million mu, and there are problems such as low number of live bacteria in fertilizer production, few varieties, unstable effects, high costs and prices. Moreover, the development and application of microbial fertilizer strains are basically limited to bacteria and fungi, and there have been no reports on the development of ciliated protozoa with high ecological diversity and high biological activity in soil microorganisms for the production of microbial fertilizers.

SUMMARY

The purpose of the present invention is to provide a ciliated protozoan that promotes plant seed germination and seedling growth, and has a significant promoting effect on plant seed germination and growth, thereby overcoming the shortcomings of the prior art.

The present invention first provides a use of ciliated protozoa, which is their application in the preparation of microbial fertilizers.

As a specific embodiment, the ciliated protozoan is *Colpoda* sp. JH2-5-4 strain, preserved in the China Center for Type Culture Collection (CCTCC) with the accession number CCTCC NO.: C202229, preservation date of Mar. 15, 2022, and preservation address at the Wuhan University Preservation Center in Wuchang District, Wuhan City, Hubei Province, China.

The *Colpoda* sp. JH2-5-4 strain has a 28S rDNA sequence of SEQ ID NO: 1 and an 18S rDNA sequence of SEQ ID NO: 2.

In another aspect, the present invention provides a microbial fertilizer containing the *Colpoda* sp. JH2-5-4 strain as described above.

The present invention also provides the application of the ciliated protozoan in promoting plant seed germination and growth.

As a specific embodiment, the plant is *Arabidopsis thaliana*.

After collecting more than 2,000 *Colpoda* sp. strains from soil samples from various parts of the country, the present invention selected highly efficient and active strains that can be used as microbial fertilizers through plant cultivation experiments. The screened ciliated protozoan can significantly shorten the seed germination time of plants and promote the survival rate of seedlings.

BRIEF DESCRIPTION OF THE DRAWINGS

FIGS. 1A-1B: Morphological features of JH2-5-4, including photos of the trophonts and cysts in different life stages, where FIG. 1A and FIG. 1B represent the trophonts and cysts in different life stages, respectively. Bar=10 μm.

FIG. 2: Electrophoretogram of the PCR amplification product of 28S rDNA using universal primers, where lane 1 is the DNA marker DL2000 (from top to bottom: 2000 bp, 1000 bp, 750 bp, 500 bp, 250 bp, 100 bp), and lane 2 is the target fragment amplified by 28S rDNA. A bright band of approximately 1800 bp can be observed after 25 minutes of electrophoresis on a 1% agarose gel following PCR amplification.

FIG. 3: Electrophoretogram of the PCR amplification product of 18S rDNA using universal primers, where lane 1 is the DNA marker DL2000 (from top to bottom: 2000 bp, 1000 bp, 750 bp, 500 bp, 250 bp, 100 bp), and lane 2 is the target fragment amplified by 18S rDNA. A bright band of approximately 1800 bp can be observed after 25 minutes of electrophoresis on a 1% agarose gel following PCR amplification.

FIG. 4A, FIG. 4B, FIG. 4C, and FIG. 4D represent photos taken at different time points, namely, Oct. 6, 2021, Oct. 26, 2021, Oct. 8, 2021, and Nov. 24, 2021, respectively.

FIG. 5A, FIG. 5B, FIG. 5C, and FIG. 5D represent photos taken at different time points, namely, Oct. 6, 2021, Oct. 26, 2021, Oct. 8, 2021, and Nov. 24, 2021, respectively.

FIG. 6A, FIG. 6B, FIG. 6C, and FIG. 6D represent photos taken at different time points, namely, Oct. 6, 2021, Oct. 26, 2021, Oct. 8, 2021, and Nov. 24, 2021, respectively.

FIG. 7A, FIG. 7B, FIG. 7C, and FIG. 7D represent photos taken at different time points, namely, Oct. 6, 2021, Oct. 26, 2021, Oct. 8, 2021, and Nov. 24, 2021, respectively.

FIG. 8A, FIG. 8B, FIG. 8C, and FIG. 8D represent photos taken at different time points, namely, 20211006, 20211026, 20211008, and 20211124.

DETAILED DESCRIPTION OF THE EMBODIMENTS

Figure 4A:
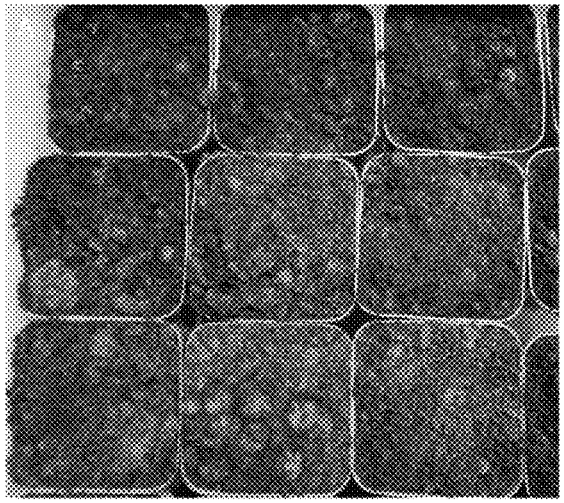
FIGS. 4A-4D: Growth process of *Arabidopsis thaliana* in the control group, where

The following detailed description of the invention is provided in conjunction with the embodiments and drawings.

Embodiment 1: Isolation and Identification of *Colpoda* sp. JH2-5-4

Approximately 200 g of soil was collected from different provinces in China. 2 g of soil was taken, wrapped in gauze, and soaked in sterilized distilled water for three cycles of boiling. The soil was soaked for approximately 24 hours, and ciliates were isolated from the soil leachate using a pipette. Double-antibiotic solution (penicillin-streptomycin) was used twice during the isolation process, followed by sterilized distilled water wash once. After washing, the isolated ciliates were fed with *Escherichia coli* bacterial suspension at OD=0.2 (wavelength 600 nm) and cultured at a constant temperature of 25° C.

JH2-5-4 strain, collected from the Diqing area of Yunnan province, had a kidney-shaped body and an oral area near the edge of the anterior vestibule, with a cytostome at the bottom. The edge in front of the oral area was serrated, and all cilia were of the same length except for two long ones (FIG. 1A). The dormant cysts of JH2-5-4 strain were spherical and often formed a large cluster after drying (FIG. 1B).

Genomic DNA was extracted from the strain and 28S rDNA and 18S rDNA sequences amplified and sequenced. After identification through NCBI database searching, it was determined to be *Colpoda* sp. and named as *Colpoda* sp. JH2-5-4 strain. The strain is stored at the China Center for Type Culture Collection under the accession number CCTCC No.: C202229, with the deposit date of Mar. 15, 2022, and the deposit address at Wuhan University Collection Center, Wuhan, Wuchang District, Hubei Province, China.

The primer sequences were as follows: F3: 5'-ACSCGCT-GRAYTTAAGCAT-3', as shown in SEQ ID NO: 3; R2: 5'-AACCTTGGAGACCTGAT-3', as shown in SEQ ID NO: 4; and the PCR amplification of 28S rDNA was carried out. The amplified fragment was 1812 bp (FIG. 2), and the sequence is shown below:

```
                                            (SEQ ID NO: 1)
5'-TGAGATCAACTCTTACTTGGATTTTCAAGGGTCGTCA

CGAGCGCACCTAACATCGCATAGAGTGCGATGCTCTTCCT

GACATATAGCCTTCGCTCTGGATAATCCAATTTCAAGGCG
```

-continued
```
GTAGTCAGTTAAAAAGAAAAGATAACTCTTCTAGGGGCAC

ATGCCGACGTCTCCAAGCTCGCTTTGAAGTGTTACCACAA

AATCCACGTCCTACTTCAGGAATATTAACCTGATTCCCTT

TTGATATCGCGTAGTCAAGCTACGAACGTATATAAAGAAG

GAATTTCCCTATATCTTAGGATCGAGTAACCCATGACCAA

TTGCTGTTCTCATGGAACCCTCCTCCACTTCGGCCTTCAA

AGTTCTCATTTGAATATTTGCTACTACCACCAAGATCTGC

ACTAGAGGCAGTTCCACCCAAGCTCACGCTAAAGGCTTCT

ACACTTGCCCCCACGCCCTCTTACTCATTAGTGCCTCATA

TTAAATTTGCACTAATGGTTGAGTATCGGCAGCACGCTTC

AGCGCCATCAATTTTCAGGGCTAATTCATTCGGCAGGTGA

GTTGTTACACACTCCTTAGCGGGTTCCGACTTCCATGGCC

ACCGTCCTGCTGTCTTTATGAATCAACACCTTTTATGGTA

TCTGATGAGCGTGCATTTGGGCGCCTTAACTCAACGTTAG

GTTCATCCCTCATCGCCAGTTCTGCTTACCAAAAACGGCC

CACTTAGAACGATACATTCTGCCCTAGAGTTCAGTTAAGA

AAACTCGAGGTTCTTACCAATTTAAAGTTTGAGAATAGGT

CAAAGGTGTTTCACCTCTGATGCCTCTAATCATTCGCTTT

ACCTAATAAAACTGCATATACGTTCCAGCTATCCTGAGAG

AAACTTCAGAGGGAACCAGCTACTAGATGGTTCGATTAGT

CTTTCGCCCCTATACTCAAGTTTGACGAACGATTTGCACG

TCAGTATCGCTACGAGCCTCCACCARAGTTTCCCCTGGCT

TCACCCTACTCAAGCATAGTTCACCATCTTTCGGGTCCTA

CCAAATATGCTCTTACTCGAACCTTTCACAAAAGATCATG

GTCGGTCGATGCTGCGGGAGTTCGGCGTACCTCACCCCTT

GGCACCTTATACTTACTTTCATTAAGCCTATGAGTTTTTG

CACTCGCAAACTCGCATATGTGATAGACTCCTTGGTCCGT

GTTTCAAGACGGGTCAGTACAAGCCGTTGTGGCAGGACCT

ATTTCCTCAGGCCAGTTTACTGTTTTGAAGGGAGATTCTA

CCAGAAGGCAGGGCTTTCTCCCAACTGACTCCAGCAAAT

GAGACCTGGTCCTGCCCTTTAACTATGAAATCCCGATAGA

GTGCCATTACATCGTAGCAGCTAGCCAATAACGTACATTA

CTACTACGAGCTGGTTCCTCACATCGGTTGCTTCATAGCT

AACATAAATCCACTTGTACTGCTTCCTCCTCAACGATTTC

AAGTCTTTTAACCCTCTTTTCAAAGTTCTTTTCACCTTTC

CTTCACAGTACTTGTTCGCTATCGGTTTCCCATAGATATT

TAGCTTTAGAAGAAGTTTATCTCCCATTTAGGGCTGCAAT

CCCAAACAACCCGACTCTTAGATAAATAACATTCGGTTCA

ATGGAAGCTACATACGGGATTTTCACCCTCTATGATGTCC

TGTTCCAAGGAACTTATGCTTCCAAATCCCCTGTTGTTAC
```

-continued
```
TCACTTTAGATTACAATTCGAAAACCGAGACGGCCTCCGA

TTCTAAACTTGAGCTATTGCCGCTTCACTCGCCGCTACTG

AGGCAATCTTCGTGA-3';
```

EukA: 5'-AACCTGGTTGATCCTGCCAGT-3', as shown in SEQ ID NO: 5; EukB: 5'-TGATCCTTCTGCAGGTT-CACCTAC-3', as shown in SEQ ID NO: 6; to perform PCR amplification of 18S rDNA, use the EukA and EukB primers. The amplified fragment is 1713 bp (FIG. 3), and the sequence is as follows:

```
                                        (SEQ ID NO: 2)
5'-GGAACCATGTCACTTCTCCTTCCTCTAGTGATAAGGT

TTACTTCTATTCCCACGATCGGGTCAAGCCCGGCCACGGT

CCTTTAGGTTCACCGGACCACTCAAAATCGGTAGGAGCGA

CGGGCGGTGTGTACAAAGGGCAGGGACGTAATCAGCACAA

GCTGATGACTTATGCTTACTAGGAATTCCTCGTTCAAGAT

CTATAATTCCAAAGATCTATCCCTAGCACGACATACATTA

TACAAGATTACCCGTACTCTTCCGAGACAGGAAAGTAAAG

CTTGTTGCATATGTCAGTGTAGCGCGCGTGCGGCCCAGGA

CATCTAAGGGCATCACAGACCTGTTATTGCCTCAAACTTC

CTTGTGCTTGCACACAAAGTCCCTCTAAGAAGTTAGCCTC

CTATTTACATAGAAGTAACTAGTTAGCAGGTTAAGGTCTC

GTTCGTTAACGGAATTAACCAGACAAATCACTCCACCAAC

TAAGAACGCCATGCACCACCACCCATAGAATCAAGAAAG

AGCTTTCAATCTGTCAATCCTAACTATGTCTGGACCTGGT

AAGTTTCCCCGTGTTGAGTCAAATTAAGCCGCAGGCTCCA

CTCCTGGTGGTGCCCTTCCGTCAATTCCTTTAAGTTTCAG

CCTTGCGACCATACTCCCCCCAGAACCCAAAGACTTTGAT

TTCTCATAAGGTGCTGATGAGGCTTAAGAAACCTCACCAA

TCCCTAGTCGGTATAGTTTATGGTTAAGACTAGGACGGTA

TCTGATCGTCTTTGATCCCCTAACTTTCGTTCTTGATTAA

TGAAAACATCCTTGGCAAATGCTTTCGCATAAGTTCGTCT

TTAATAAATCCAAGAATTTCACCTCTGACAATTAAATACG

GATGCCCCCAACTGTCCCTATTAATCATTACTTTGACCTC

AAGAAACCAACAAATAGGTCAAAGTCCTATTCCATTATTC

CATGCTGCAGTATCCAAGCAATTGCCTGCCTGAAACACTC

TAATTTTTTCAAAGTAAAGTGTATGATCCACTAGCCGACC

ACTGAAGGACGTGCTAGCTTCCCATACGGATGACCAGGCT

CCTGAACCGACTGCGAGAGCCGTGAACAGCGCCGGCCAGA

AATTCAACTACGAGCTTTTTAACTGCAACAACTTTAATAT

ACGCTATTGGAGCTGGAATTACCGCGGCTGCTGGCACCAG

ACTTGCCCTCCAATTGTTACTCGATAAGTGGTTTAAATTG

TTCTCATTGCAATCTCGCAACCCCATGTGGGGCCCGAGTT
```

-continued
```
GTTATTTCTTGTCACTACCTCCCTGAATTAGGATTGGGTA

ATTTACGCGCCTGCTGCCTTCCTTAGATGTGGTAGCCATT

TCTCAGGCTCCCTCTCCGGAATCGAACCCTAATTCCCCGT

TACCCGTGATCGCCATGGTAGTCCAATACACTACCATCGA

AAGCTGATAGGGCAGAAACTTGAACGATTCGTCGCGGCGA

GGCCGCGATCCGCTCAGTTATTATGAATCATCACTATCCT

GTTGCCAGGGTTAGTTTAATATCTAATAAATACAACCCTT

CCGAAAAGTCAGGTTTGACAGCATGTATTAGCTCTAGAAT

TACTACGGTTATCCATGTAGAAGAAAATAATCGAATAAAC

TATAACTGTTTTAATGAGCCATTCGCAGTTTCGCTGTATA

TAACTTATACTTAGACATGCAGGCGTAGTCATAGCC-3'.
```

Example 2: Study on the Promotion of Plant Seed Germination by *Colpoda* JH2-5-4

Among the numerous strains of *Colpoda* we isolated, we selected *Colpoda* from four regions, namely Qingdao in Shandong, Hegang in Heilongjiang, Bencuo in Naqu, Tibet, and Diqing in Yunnan, according to climate differences for plant cultivation experiments.

*Arabidopsis* seeds were synchronized by dark incubation at 4° C. for 7 days. The seeds were disinfected in 75% ethanol for 10 minutes and suspended in 0.1% agarose. Soil and an appropriate amount of distilled water were mixed evenly and subjected to high-pressure steam sterilization to remove preexisting soil microorganisms. Gauze was cut to a suitable size and placed at the bottom of each pot, and the hydrated soil was aliquot and placed into each pot for later use. One seed was picked up with a pipette and planted in each pot, with 9 seeds per pot and 20 replicated pots in total. The control group was treated with only *Escherichia coli* liquid with a volume and density corresponding to that of the treatment group. The experimental group was treated with ~20,000 *Colpoda* added to the pots with seeds. The pots were labeled and put onto two trays, one for the experimental group and the other for the control group. The pots were placed in different culture chambers with a temperature of 25° C., a 16/8 h (light/dark) cycle, humidity of 65%, and light intensity of 4950 lux. During the cultivation period, the soil conditions were monitored, and the plants were photographed and watered. Every 2 weeks, the plants were irrigated with 1/10 MS medium to add a small amount of mineral nutrients.

The results showed that *Colpoda* from Diqing, Yunnan had the best effect on promoting *Arabidopsis* seed germination, with a germination rate as high as 87.77% (Table 1).

TABLE 1

Data for improving *Arabidopsis* germination rate with different regions-screened *Colpoda*.

| Strain No. | Sample ID | | | | | | | | | | | | | | | | | | | | Surviving Rate % |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | |
| Shandong Qingdao *Colpoda*-RZ04A | 9 | 8 | 9 | 7 | 9 | 8 | 5 | 6 | 7 | 8 | 6 | 7 | 8 | 9 | 8 | 9 | 5 | 7 | 9 | 9 | 85.00 |
| Heilongjiang Hegang *Colpoda*-PJ01A01 | 8 | 7 | 7 | 6 | 8 | 6 | 2 | 5 | 7 | 9 | 7 | 7 | 8 | 9 | 9 | 7 | 8 | 7 | 6 | 5 | 76.67 |
| Tibet Bengcuo Naqu *Colpoda*-LHA0612 | 9 | 3 | 4 | 7 | 5 | 8 | 9 | 7 | 9 | 7 | 8 | 7 | 8 | 6 | 7 | 7 | 7 | 5 | 5 | 2 | 72.22 |
| Yunnan Diqing *Colpoda*-JH2-5-4 | 9 | 8 | 7 | 9 | 9 | 9 | 8 | 8 | 7 | 9 | 8 | 9 | 8 | 6 | 7 | 9 | 9 | 5 | 6 | 8 | 87.77 |
| Control Bacteria | 4 | 0 | 1 | 0 | 6 | 0 | 3 | 1 | 6 | 4 | 5 | 2 | 4 | 1 | 3 | 4 | 6 | 5 | 6 | 1 | 34.44 |

Example 3: Study on the Promotion of Plant Growth by *Colpoda* JH2-5-4

A comparative test on plant cultivation was conducted using *Colpoda* JH2-5-4 vs. *Colpoda* strains from Qingdao (Shandong province), Hegang (Heilongjiang province), and Bengcuo (Naqu city, Tibet).

Example 3: Study on Promoting Plant Growth with *Colpoda* JH2-5-4

*Arabidopsis* seeds were synchronized by incubating in the dark at 4° C. for 7 days. The seeds were disinfected by immersing in 75% ethanol for 10 minutes and then resuspended in 0.1% agarose. Soil and distilled water were mixed and sterilized by high-pressure steam to eliminate pre-existing soil organisms. Gauze was cut to the appropriate size and placed at the bottom of each flowerpot, and the soaked soil was evenly distributed and placed in the flowerpot for later use. One seed was planted in each flowerpot using a micropipette, and each flowerpot had one seed, with a total of 9 replicates. The control group only added the same volume and density of *E. coli* solution as the treatment group, while the experimental group added ~20,000 *Colpoda* sp. to each flowerpot containing seeds. The flowerpots were labeled and placed in two trays for the experimental and control groups, respectively. They were placed in an incubator at 25° C., 16/8 h (light/dark), and 65% humidity, with a light intensity of 4950 lux. The soil conditions and plant growth were observed and recorded by taking photos during the cultivation period, and water was given as needed. Additionally, every two weeks, 1/10 MS culture medium was added to the plants to supply them with a small amount of mineral nutrients.

Figure 4B:
Figure 4C:
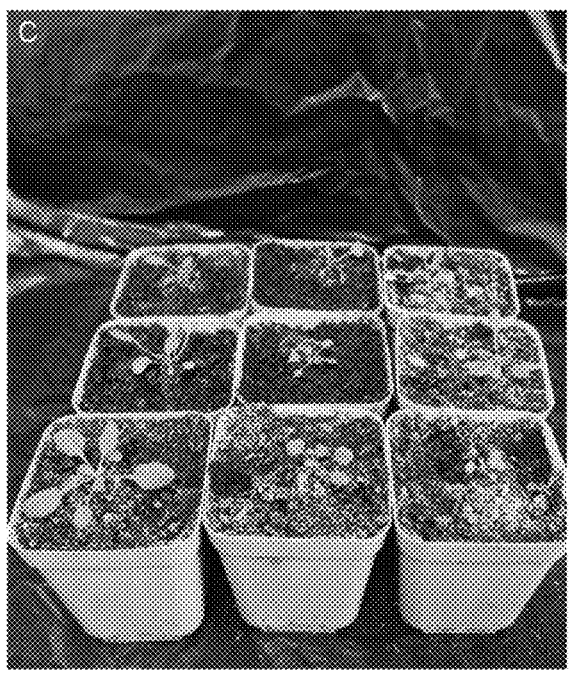
Figure 4D:
Figure 5A:
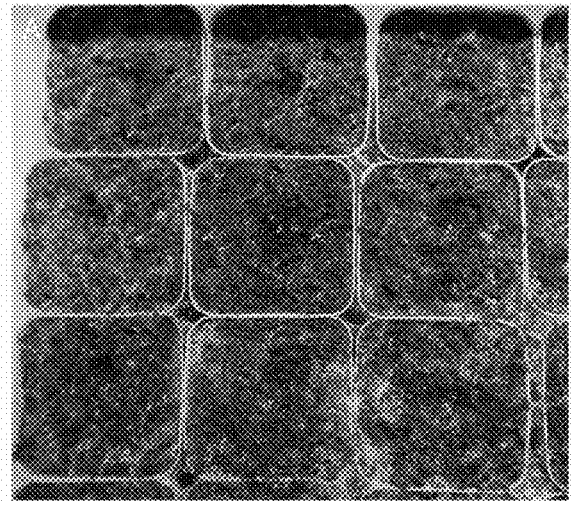
FIGS. 5A-5D: Effects of *Colpoda* JH2-5-4 (collected from Diqing, Yunnan) on the growth of *Arabidopsis thaliana*, where
Figure 5B:
Figure 5C:
Figure 5D:
Figure 6A:
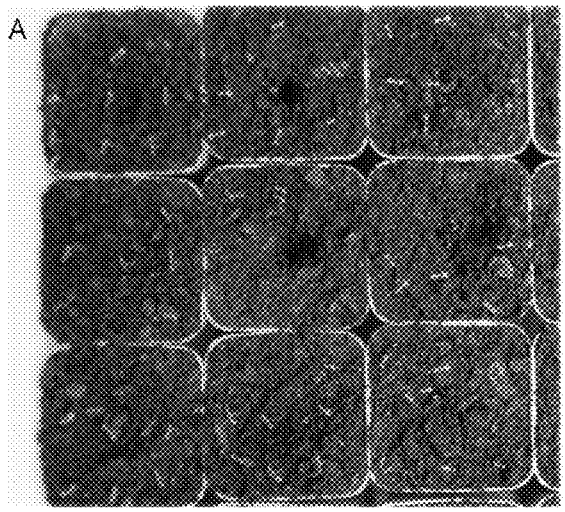
FIGS. 6A-6D: Effects of *Colpoda* PJ01A01 (collected from Hegang, Heilongjiang) on the growth of *Arabidopsis thaliana*, where
Figure 6B:
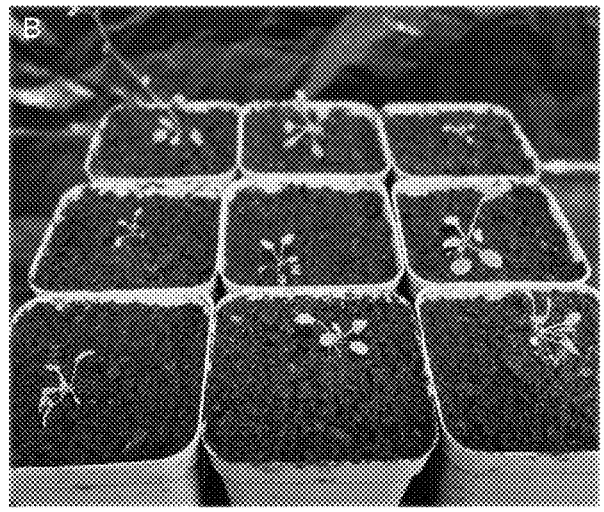
Figure 6C:
Figure 6D:
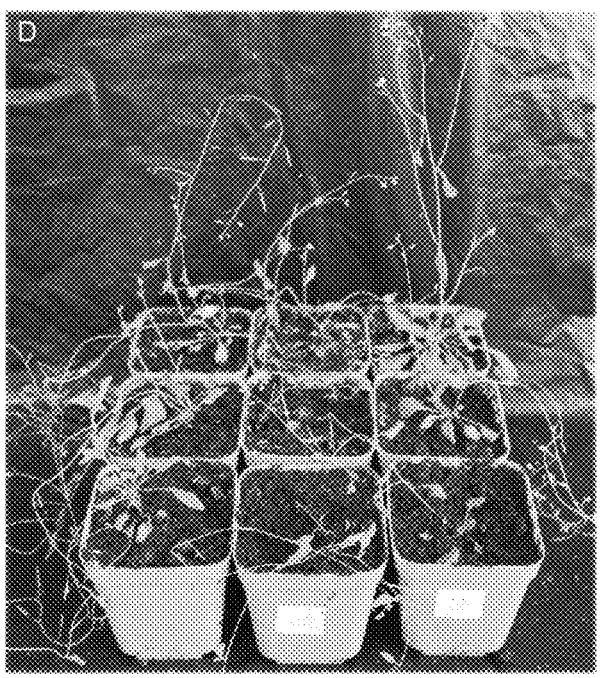
Figure 7A:
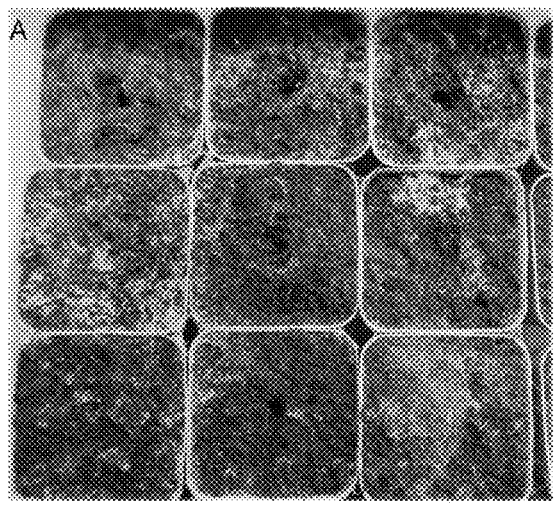
FIGS. 7A-7D: Effects of *Colpoda* LHA0612 (collected from Bengcuo, Naqu, Tibet) on the growth of *Arabidopsis thaliana*, where
Figure 7B:
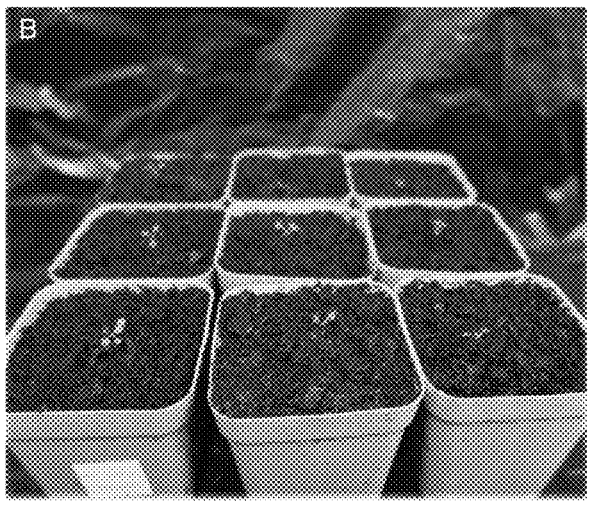
Figure 7C:
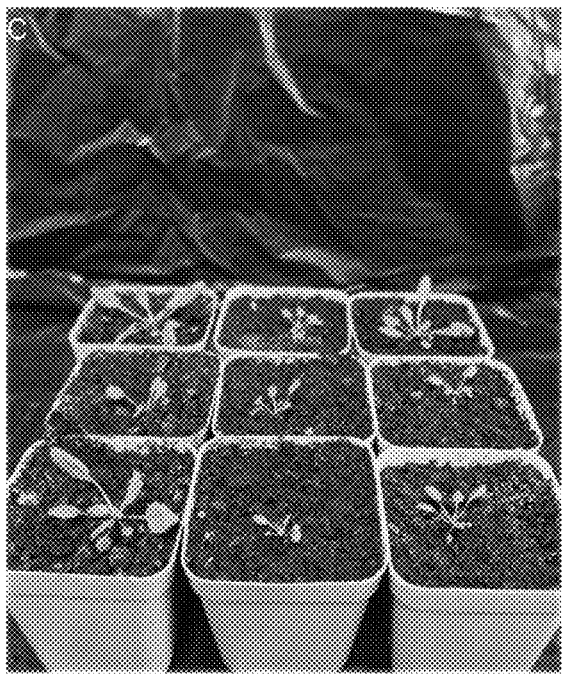
Figure 7D:
Figure 8A:
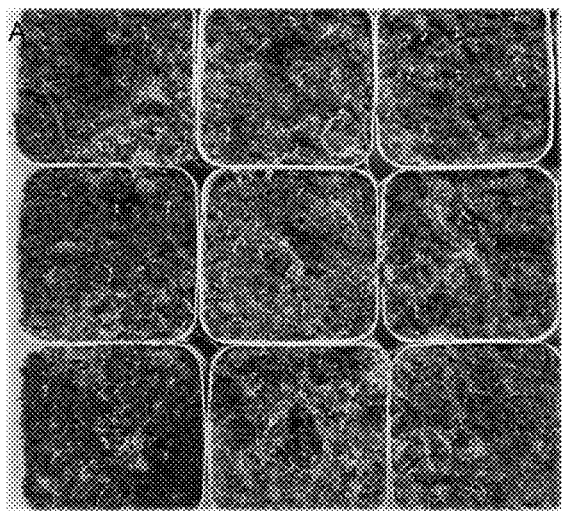
FIGS. 8A-8D: Effects of *Colpoda* RZO4A (collected from Qingdao, Shandong) on the growth of *Arabidopsis thaliana*, where
Figure 8B:
Figure 8C:
Figure 8D:

The records of *Arabidopsis* growth state showed that the growth rate of *Arabidopsis* plants with *Colpoda* sp. JH2-5-4 added was significantly higher than that of the control group (FIGS. 4A-4D to FIGS. 8A-8D).

Therefore, the *Colpoda* sp. JH2-5-4 screened by the present invention can significantly promote plant germination and growth and can be used as an active non-bacterial microorganism in microbial fertilizers.

What is claimed is:

1. A method for promoting the germination of *Arabidopsis thaliana* seeds using ciliated protozoa, comprising the steps of:
 a) synchronizing the *Arabidopsis thaliana* seeds by dark incubation at 4°C for 7 days;
 b) disinfecting the synchronized *Arabidopsis thaliana* seeds in 75% ethanol for 10 minutes and suspending the plant seeds in 0.1% agarose;
 c) mixing soil and distilled water, and then subjecting the soil and distilled water to high-pressure steam sterilization to remove preexisting soil microorganisms producing hydrated soil;
 d) cutting gauze and placing the gauze at the bottom of each pot of a plurality of pots, wherein the plurality of pots consists of 20 pots;
 e) aliquoting the hydrated soil into each pot of the plurality of pots;
 f) placing nine seeds in each pot of the plurality of pots;
 g) treating the hydrated soil in each pot of the plurality of pots with an *Escherichia coli* suspension;
 h) treating each pot of the plurality of pots with approximately 20,000 ciliated protozoa;
 i) labeling each pot, and placing each pot of the plurality of pots onto a tray of a plurality of trays;
 j) placing each tray of the plurality of trays in a different culture chamber with a temperature of 25° C., a 16/8 hour (light/dark) cycle, humidity of 65%, and light intensity of 4950 lux; and
 k) photographing and watering any *Arabidopsis thaliana* plants,
 wherein the ciliated protozoa are a *Colpoda* species with a preservation number of China Center for Type Culture Collection No. C202229.

* * * * *

SEQUENCE LISTING

```
Sequence total quantity: 6
SEQ ID NO: 1              moltype = DNA  length = 1812
FEATURE                   Location/Qualifiers
source                    1..1812
                          mol_type = other DNA
                          organism = Colpoda sp.
SEQUENCE: 1
tgagatcaac tcttacttgg attttcaagg gtcgtcacga gcgcacctaa catcgcatag   60
agtgcgatgc tcttcctgac atatagcctt cgctctggat aatccaattt caaggcggta  120
gtcagttaaa aagaaaagat aactcttcta ggggcacatg ccgacgtctc caagctcgct  180
ttgaagtgtt accacaaaat ccacgtccta cttcaggaat attaacctga ttcccttttg  240
atatcgcgta gtcaagctac gaacgtatat aaagaaggaa tttccctata tcttaggatc  300
gagtaaccca tgaccaattg ctgttctcat ggaaccctcc tccacttcgg ccttcaaagt  360
tctcatttga atatttgcta ctaccaccaa gatctgcact agaggcagtt ccacccaagc  420
tcacgctaaa ggcttctaca cttgccccca cgccctctta ctcattagtg cctcatatta  480
aatttgcact aatggttgag tatcggcagc acgcttcagc gccatcaatt ttcagggcta  540
attcattcgg caggtgagtt gttacacact ccttagcggg ttccgacttc catggccacc  600
gtcctgctgt ctttatgaat caacaccttt tatggtatct gatgagcgtg catttgggcg  660
ccttaactca acgttaggtt catccctcat cgccagttct gcttaccaaa aacggcccac  720
ttagaacgat acattctgcc ctagagttca gttaagaaaa ctcgaggttc ttaccaattt  780
aaagtttgag aataggtcaa aggtgtttca cctctgatgc ctctaatcat tcgctttacc  840
taataaaact gcatatacgt tccagctatc ctgagagaaa cttcagaggg aaccagctac  900
tagatggttc gattagtctt tcgcccctat actcaagttt gacgaacgat ttgcacgtca  960
gtatcgctac gagcctccac caragttcc cctggcttca ccctactcaa gcatagttca 1020
ccatctttcg ggtcctacca aatatgctct tactcgaacc tttcacaaaa gatcatggtc 1080
ggtcgatgct gcgggagttc ggcgtacctc acccctttggc accttatact tactttcatt 1140
aagcctatga gttttgcac tcgcaaactc gcatatgtga tagactcctt ggtccgtgtt 1200
```

```
tcaagacggg tcagtacaag ccgttgtggc aggacctatt tcctcaggcc agtttactgt    1260
tttgaaggga gattctacca gaaggcaggg ctttctccca actgactcca gcaaaatgag    1320
acctggtcct gcccttttaac tatgaaatcc cgatagagtg ccattacatc gtagcagcta    1380
gccaataacg tacattacta ctacgagctg gttcctcaca tcggttgctt catagctaac    1440
ataaatccac ttgtactgct tcctcctcaa cgatttcaag tcttttaacc ctcttttcaa    1500
agttcttttc acctttcctt cacagtactt gttcgctatc ggtttcccat agatatttag    1560
ctttagaaga agtttatctc ccatttaggg ctgcaatccc aaacaacccg actcttagat    1620
aaataacatt cggttcaatg gaagctacat acgggatttt caccctctat gatgtcctgt    1680
tccaaggaac ttatgcttcc aaatcccctg ttgttactca ctttagatta caattcgaaa    1740
accgagacgg cctccgattc taaacttgag ctattgccgc ttcactcgcc gctactgagg    1800
caatcttcgt ga                                                        1812

SEQ ID NO: 2           moltype = DNA  length = 1713
FEATURE                Location/Qualifiers
source                 1..1713
                       mol_type = other DNA
                       organism = Colpoda sp.
SEQUENCE: 2
ggaaccatgt cacttctcct tcctctagtg ataaggttta cttctattcc cacgatcggg     60
tcaagcccgg ccacggtcct ttaggttcac cggaccactc aaaatcggta ggagcgacgg    120
gcggtgtgta caaagggcag ggacgtaatc agcacaagct gatgacttat gcttactagg    180
aattcctcgt tcaagatcta taattccaaa gatctatcc tagcacgaca tacattatac    240
aagattaccc gtactcttcc gagacaggaa agtaaagctt gttgcatatg tcagtgtagc    300
gcgcgtgcgg cccaggacat ctaagggcat cacagacctg ttattgcctc aaacttcctt    360
gtgcttgcac acaaagtccc tctaagaagt tagcctccta tttacataga agtaactagt    420
tagcaggtta aggtctcgtt cgttaacgga attaaccaga caaatcactc caccaactaa    480
gaacggccat gcaccaccac ccatagaatc aagaaagagc tttcaatctg tcaatcctaa    540
ctatgtctga acctggtaag tttcccgtg ttgagtcaaa ttaagccgca ggctccactc    600
ctggtggtgc ccttccgtca attccttaa gtttcagcct tgcgaccata ctccccccag    660
aacccaaaga ctttgatttc tcataaggtc gtgatgaggc ttaagaaacc tcaccaatcc    720
ctagtcggta tagtttatgg ttaagactag gacggtatct gatcgtcttt gatcccctaa    780
cttttcgttct tgattaatga aaacatcctt ggcaaatgct ttcgcataag ttcgtctta    840
ataaatccaa gaatttcacc tctgacaatt aaatacggat gcccccaact gtccctatta    900
atcattactt tgacctcaag aaaccaacaa ataggtcaaa gtcctattcc attattccat    960
gctgcagtat ccaagcaatt gcctgcctga acactctaa ttttttcaaa gtaaagtgta   1020
tgatccacta gccgaccact gaaggacgtg ctagcttccc atacggatga ccaggctcct   1080
gaaccgactg cgagagccgt gaacagcgcc ggccagaaat tcaactacga gcttttaac   1140
tgcaacaact ttaatatacg ctattggagc tggaattacc gcggctgctg gcaccagact   1200
tgccctccaa ttgttactcg ataagtggtt taaattgttc tcattgcaat ctcgcaaccc   1260
catgtgggc ccgagttgtt atttcttgtc actacctccc tgaattagga ttgggtaatt   1320
tacgcgcctg ctgcccttcct tagatgtggt agccatttct caggctccct ctccggaatc   1380
gaaccctaat tccccgttac ccgtgatcgc catggtagtc caatacacta ccatcgaaag   1440
ctgataggc agaaacttga acgattcgtc gcggcgaagc cgcgatccgc tcagttatta   1500
tgaatcatca ctatcctgtt gccagggtta gtttaatatc taataaatac aacccttccg   1560
aaaagtcagg tttgacagca tgtattagct ctagaattac tacgttatc catgtagaag   1620
aaaataatcg aataaactat aactgtttta atgagccatt cgcagtttcg ctgtatataa   1680
cttatactta gacatgcagg cgtagtcata gcc                                1713

SEQ ID NO: 3           moltype = DNA  length = 19
FEATURE                Location/Qualifiers
source                 1..19
                       mol_type = other DNA
                       organism = synthetic construct
SEQUENCE: 3
acscgctgra yttaagcat                                                   19

SEQ ID NO: 4           moltype = DNA  length = 17
FEATURE                Location/Qualifiers
source                 1..17
                       mol_type = other DNA
                       organism = synthetic construct
SEQUENCE: 4
aaccttggag acctgat                                                     17

SEQ ID NO: 5           moltype = DNA  length = 21
FEATURE                Location/Qualifiers
source                 1..21
                       mol_type = other DNA
                       organism = synthetic construct
SEQUENCE: 5
aacctggttg atcctgccag t                                                21
```

```
SEQ ID NO: 6            moltype = DNA  length = 24
FEATURE                 Location/Qualifiers
source                  1..24
                        mol_type = other DNA
                        organism = synthetic construct
SEQUENCE: 6
tgatccttct gcaggttcac ctac                                              24
```